(12) United States Patent
Peterson et al.

(10) Patent No.: US 6,613,755 B2
(45) Date of Patent: Sep. 2, 2003

(54) ANTIMICROBIAL SKIN PREPARATIONS CONTAINING ORGANOSILANE QUATERNARIES

(75) Inventors: William R. Peterson, Phoenix, AZ (US); David Giaccio, Phoenix, AZ (US); Renee E. Berman, Chandler, AZ (US)

(73) Assignee: Coating Systems Laboratories, Inc., Chandler, AZ (US)

( * ) Notice: Subject to any disclaimer, the term of this patent is extended or adjusted under 35 U.S.C. 154(b) by 0 days.

(21) Appl. No.: 10/112,177

(22) Filed: Mar. 29, 2002

(65) Prior Publication Data

US 2002/0141959 A1 Oct. 3, 2002

Related U.S. Application Data

(63) Continuation of application No. 09/526,701, filed on Mar. 15, 2000.
(60) Provisional application No. 60/124,504, filed on Mar. 16, 1999.

(51) Int. Cl.[7] .............................................. A61K 31/695
(52) U.S. Cl. .......................... 514/63; 556/413; 424/63; 424/609
(58) Field of Search ........................... 556/413; 514/63; 424/63, 609

(56) References Cited

U.S. PATENT DOCUMENTS

| | | |
|---|---|---|
| 3,560,385 A | 2/1971 | Roth |
| 3,730,701 A | 5/1973 | Isquith et al. |
| 3,794,736 A | 2/1974 | Abbott et al. |
| 3,817,739 A | 6/1974 | Abbott et al. |
| 3,860,709 A | 1/1975 | Abbott et al. |
| 3,865,728 A | 2/1975 | Abbott et al. |
| 3,940,430 A | 2/1976 | Brenner et al. |
| 4,005,025 A | 1/1977 | Kinstedt |
| 4,005,028 A | 1/1977 | Heckert et al. |
| 4,005,030 A | 1/1977 | Heckert et al. |
| 4,005,118 A | 1/1977 | Heckert et al. |
| 4,013,574 A | 3/1977 | Leikhim et al. |
| 4,161,518 A | 7/1979 | Wen et al. |
| 4,282,366 A | 8/1981 | Eudy |
| 4,361,273 A | 11/1982 | Levine et al. |
| 4,394,378 A | 7/1983 | Klein |
| 4,395,454 A | 7/1983 | Baldwin |
| 4,406,892 A | 9/1983 | Eudy |
| 4,408,996 A | 10/1983 | Baldwin |
| 4,411,928 A | 10/1983 | Baldwin |
| 4,414,268 A | 11/1983 | Baldwin |
| 4,421,796 A | 12/1983 | Burril et al. |
| 4,425,371 A | 1/1984 | Stratmann et al. |
| 4,467,013 A | 8/1984 | Baldwin |
| 4,564,456 A | 1/1986 | Homan |
| 4,567,039 A | 1/1986 | Stadnick et al. |
| 4,615,882 A | 10/1986 | Stockel |
| 4,631,297 A | 12/1986 | Battice et al. |
| 4,682,992 A | 7/1987 | Fuchs |
| 4,781,974 A | 11/1988 | Bouchette et al. |
| 4,797,420 A | 1/1989 | Bryant |
| 4,842,766 A | 6/1989 | Blehm et al. |
| 4,845,256 A | 7/1989 | Mebes et al. |
| 4,847,088 A | 7/1989 | Blank |
| 4,865,844 A | 9/1989 | Blank et al. |
| 4,866,192 A | 9/1989 | Plueddemann et al. |
| 4,908,355 A | 3/1990 | Gettings et al. |
| 4,933,327 A | 6/1990 | Plueddemann et al. |
| 4,985,023 A | 1/1991 | Blank et al. |
| 5,013,459 A | 5/1991 | Gettings et al. |
| 5,019,173 A | 5/1991 | Gettings et al. |
| 5,145,596 A | 9/1992 | Blank et al. |
| 5,281,414 A | 1/1994 | Stockel |
| 5,359,104 A | 10/1994 | Higgs et al. |
| 5,399,737 A | 3/1995 | Park et al. |
| 5,411,585 A | 5/1995 | Avery et al. |
| 5,954,869 A | 9/1999 | Elfersy et al. |
| 6,113,815 A | 9/2000 | Elfersy et al. |
| 6,120,587 A | 9/2000 | Elfersy et al. |

FOREIGN PATENT DOCUMENTS

CA        1217004        1/1987

*Primary Examiner*—Samuel Barts
(74) *Attorney, Agent, or Firm*—Townsend and Townsend and Crew LLP (57) ABSTRACT

A method for application to the skin of aqueous compositions containing antimicrobial organosilane quaternary ammonium compounds, which remain on the skin, are substantive to it and reduce or eliminate bacteria, viruses and fungi present and prevent future contamination by their presence and substantive character. All formulations are aqueous solutions which may be scented and/or colored and all contain a water soluble, organosilicon quaternary ammonium compound or mixture thereof; specifically 3-(trimethoxysilyl)-propyloctadecyl-dimethyl ammonium chloride or 3-(trimethoxysilyl)propyldidecylmethyl ammonium chloride and the trisilanol, polysiloxanol and water soluble polysiloxane derivatives thereof.

23 Claims, 5 Drawing Sheets

Figure 1

Reduction of Bacterial Concentration on Human Skin over 8 Hour Period

Effect of Pig with Ammonium Skin Treated Quaternary Organosilane Solution on *Staphylococcus Aureus*

——— Untreated Skin
– – – – Treated Skin

Rinsing Effect with Ammonium Organosilane Over 30 min.

Figure 4 on Pig Skin Treated Quaternary in Reducing *Staphylococcus Aureus*

Figure 5

Reduction of *Staphylococcus Aureus* with Increased Surface Concentration of Quaternary Ammonium Organosilane

ANTIMICROBIAL SKIN PREPARATIONS CONTAINING ORGANOSILANE QUATERNARIES

CROSS-REFERENCE TO RELATED APPLICATION

This application is related to U.S. Provisional Patent Application No. 60/124,504, filed Mar. 16, 1999, and claims all benefits legally available therefrom. Provisional Patent Application No. 60/124,504 is hereby incorporated by reference for all purposes capable of being served thereby.

BACKGROUND OF THE INVENTION

1. Field of the Invention

This invention relates to the preparation of aqueous formulations containing monomeric, dimeric and oligomeric water soluble organosilane species having a silicon-bonded quaternary ammonium halide functionality and hydrolyzable alkoxy groups and for their application to human skin wherein the monomeric and oligomeric species react on the skin to provide an insoluble, polymeric antimicrobial treatment which is substantive to the skin, is not removed by rinsing, retains its microbial activity while present on the skin and which moisturizes the skin by its presence.

2. Description of the Prior Art

Organosilanes containing quaternary ammonium halides and hydrolyzable alkoxy groups bonded to silicon have been employed in a wide variety of applications. The hydrolyzable groups enable these compounds to form bonds to substrates that contain hydroxy, alkoxy, oxide and similar reactive moieties. Organosilanes have been used to waterproof masonry and brick surfaces, as paint additives, fabric treatments and for surface modification of substrates that enhance miscibility in organic solvents or enable subsequent operations to be conducted on the substrate such as dyeing or painting.

Organosilane quaternary nitrogen compounds have also been employed effectively in eliminating and reducing bacterial, viral and fungal contamination when applied to a variety of surfaces including metal, glass, plastics, rubber, ceramics and fabrics including cellulose, cotton, acetates and nylon.

For health, safety and economical reasons, it is most desirable to apply such antimicrobial quaternized organosilanes from an aqueous medium, which may contain additives and components the purpose of which is to increase stability, provide scent and color, and improve performance.

The stability of aqueous solutions of organosilanes varies from minutes to hours for simple organosilanes such as methyltrimethoxysilane and to weeks for aminoalkylsilanes such as 3-aminopropyltrimethoxysilane. The instability in water of alkoxyorganosilanes is due to intermolecular condensation of the silanol groups generated through hydrolysis of the alkoxy groups to form siloxanes, which on obtaining a certain molecular weight become insoluble in water and precipitate from solution. It is well known to those skilled in the art that adjustment of the pH with acids or bases or the addition of certain surfactants will increase or decrease the rate of self-condensation.

Commercial quaternary ammonium organosilanes are available as 42% active material in methanol under the trademark Dow Coming 5700 (3-(trimethoxysilyl) propyldimethyloctadecyl ammonium chloride) by Aegis Environmental Management, Inc. of Midland, Mich. and Requat 1977 (3-(trimethoxysilyl)-propyldidecylmethyl ammonium chloride) by Sanitized Inc. of New Preston, Conn. Octadecyldimethyl(3-trimethoxysilylpropyl) ammonium chloride (Cat. No. SIO6620.0) as a 60% active solution in methanol, tetradecyldimethyl(3-trimethoxysilylpropyl) ammonium chloride (Cat. No. SIT7090.0) as a 50% solution in methanol and didecylmethyl(3-trimethoxysilylpropyl) ammonium chloride (Cat. No. SID3392.0) as a 42% solution in methanol are offered by Gelest, Inc. of Tullytown, Pa. They are often applied from solvent solutions such as lower alcohols.

Organosilicon ammonium compounds were first taught by Roth in U.S. Pat. No. 3,560,385. The use of these compounds for antimicrobial purposes is taught in U.S. Pat. No. 3,730,701 to Isquith et al. They teach that neutral to alkaline pH values were more effective in algae control, but no claims for stability of aqueous solutions were made.

Algae inhibition was also taught in U.S. Pat. Nos. 3,794,736 and 3,860,709. The inhibition of algae growth on solid surfaces such as cellulose acetate following treatment with organosilane quaternary ammonium materials was described by Abbott et al. in U.S. Pat. No. 3,817,739. Abbott et al. in U.S. Pat. No. 3,865,728 again describes algicidal reduction on fibrous materials including polyesters as well as cellulose acetate. G. Kinstedt in U.S. Pat. No. 4,005,025 claims organosilane quaternaries as being useful in imparting soil release properties to hard surfaces in detergent applications such as dishwashing liquids and general hard surface cleaners, but makes no claims for antimicrobial activity.

U.S. Pat. No. 4,005,028 to Heckert et al. similarly teaches detergent compositions containing zwitterionic or ampholytic detergents and quaternized organosilanes. Similarly, U.S. Pat. No. 4,005,030 by D. Heckert and D. Watt teach detergent formulations useful as oven cleaners, window cleaners or toiler bowl cleaners. No antimicrobial claims are present in the '025, '028 and '030 Patents.

In U.S. Pat. No. 4,282,366 organosilicon ammonium compounds are used to render paper substrates resistant to growth of microorganisms. Similarly, Klein in U.S. Pat. No. 4,394,378 claims 3-(trimethoxysilyl)propyldidecylmethyl ammonium chloride as effective against bacteria and fungi on siliceous surfaces, wood, metal, leather, rubber, plastic and textiles.

Other applications for these compounds include paint additives and shoe treatments in U.S. Pat. No. 4,393,378, dentifrice additives in U.S. Pat. No. 4,161,518, and in contact lens disinfectant solution in U.S. Pat. No. 4,615,882. Canadian Patent No. 1,217,004 to Hardy teaches these compounds are antimicrobial when added to bleach such as sodium hypochlorite and can be used as hard surface cleaners.

U.S. Pat. No. 4,406,892 describes treatment of cellulosic fabrics to prevent the growth of disease causing organisms. Similarly, Burril et al. in U.S. Pat. No. 4,421,796 teach a method of treating textile fibers with a mixture of quaternized organosilane compositions in an emulsion containing polydimethylsiloxanes to improve removal of oily soil.

In U.S. Pat. No. 4,467,013 3-(trimethoxysilyl) propyldimethyloctadecyl ammonium chloride is taught as being useful in the treatment of surgical gowns, dressings and bandages. Homan in U.S. Pat. No. 4,564,456 utilizes organosilicon quaternary ammonium compounds to treat water and inhibit corrosion and metal deposition. Hair conditioning compositions containing 3-(trimethoxysilyl) propyl-dimethyloctadecyl ammonium chloride, when applied at pH 8–10 causing the hair to swell is taught by Stadnick in U.S. Pat. No. 4,567,039.

Aqueous emulsions formed by the use of certain organofunctional cationic silanes, including quaternary ammonium organosilanes such as 3-(trimethoxysilyl)propyldimethyloctadecyl ammonium chloride, are taught by Blehm et al. in U.S. Pat. No. 4,361,273. The disclosed oil-in-water emulsions allow the transfer of water immiscible liquids and silanes to the surface of certain substrates with the avoidance of any subsequent rewetting or resolubilization of the silane or water immiscible liquid and its subsequent loss from the surface. The water immiscible liquid utilized to prevent resolubilizing of the cationic silane away from the substrate may be silicone oils, waxes, hydrocarbons, glycols or aliphatic alcohols. The preparation of these emulsions utilize co-surfactants such as nonionic and cationic surfactants and require a homogenizer using high shear conditions and teach that the quaternized organosilane does not hydrolyze to the silanol while in its emulsion form and thus does not polymerize to an insoluble siloxane. These emulsions require a water immiscible liquid as described above with which the quaternized organosilane associates, and that a sufficient shear force, requiring specialized mixers, is necessary to form the emulsion they teach. Blehm et al. teaches the prepared emulsion is utilized to transfer the unhydrolyzed quaternized organosilane to the surface where it is protected against resolubilization by the water immiscible component.

The use of similar oil-in-water emulsion compositions in treating acne vulgaris and ringworm is taught in U.S. Pat. No. 4,908,355 to Gettings & White. This patent teaches a method of treating skin disorders through topical application to the epidermis of an oil-in-water emulsion in which there is a quaternary ammonium organosilane, specifically 3-(trimethoxysilyl)propyldimethyloctadecyl ammonium chloride and a low viscosity, low molecular weight water immiscible liquid silicone fluid, which causes the quaternized silane to penetrate the follicular orifices. The volatile silicone fluid is for the purpose of driving the silane into sebaceous glands and destroying the staphylococcal group of bacteria that may reside there. The formation of these emulsions are essentially the formulations taught in the foregoing '273 patent. This patent teaches the quaternized silane can be used neat, in an organic solvent or in aqueous solvent solutions. It further teaches a water immiscible component such as an oil, wax or grease must be present and included in the compositions applied to the skin. It does not teach homogeneous aqueous solutions of the quaternary ammonium organosilane nor demonstrate substantiveness and efficacy on skin. The ability of the silane to be applied directly to the skin from aqueous solutions and the ability for the silane to remain on the skin and continue to be antimicrobially active even after repeated rinsings or washings is not taught.

Glass beads treated with organosilane quaternary compounds are described in U.S. Pat. No. 4,682,992 as being used in air filters where antimicrobial qualities are desired. U.S. Pat. No. 4,781,974 teaches wet towelettes having as organosilicon quaternary ammonium compound substantive to the fibers, but does not teach it being transferred to surfaces or skin. Bryant in U.S. Pat. No. 4,797,420 teaches a formulation containing an alkyl dimethyl benzyl ammonium chloride, a nonionic surfactant and a lower alcohol such as isopropanol in water which is used as a disinfectant formulation.

U.S. Pat. No. 4,847,088 to Blank teaches a quaternary organosilane composition such as 3-(trimethoxysilyl) propyldimethyloctadecyl ammonium chloride when combined with an acid in water will increase the antimicrobial effect. Similar antimicrobial properties are claimed in U.S. Pat. No. 5,013,459 for a method and device to dispense ophthalmic fluids, the porous medium of which has been previously treated with an organosilicon quaternary ammonium material.

U.S. Pat. No. 5,411,585 to Avery et al. teaches further methods for the production of stable hydrolyzable organosilane quaternary ammonium compounds to render surfaces antimicrobial when applied as ingredients in hard surface cleaners.

Stabilized aqueous organosilane solutions, including quaternary ammonium organosilane compounds, with stability of weeks to months, are taught by Elfersy et al. in U.S. Pat. No. 5,954,869. These compositions contain a polyol molecule having at least two hydroxy groups which are separated by no more than three intervening atoms and the organosilane. These compositions may be used to coat a food article, a fluid container or a latex medical article. Sugars are the most common stabilizer taught in this patent.

The prior art and open literature disclose the antimicrobial properties of quaternary ammonium organosilanes against a wide range of pathogens including, but not limited to:

Bacteria:
   Gram Positive Bacteria:
      *Citrobacter freundii*
      *Citrobacter diversus*
      *Corynebacterium diptheriae*
      *Diplococcus pneumoniae*
      *Micrococcus* sp. (I)
      *Micrococcus* sp. (II)
      *Micrococcus* sp. (III)
      *Mycobacterium* spp.
      *Staphylococcus albus*
      *Staphylococcus aureus*
      *Staphylococcus citrens*
      *Staphylococcus epidermidis*
      *Streptococcus faecalis*
      *Streptococcus pyogenes*
   Gram Negative Bacteria:
      *Acinetobacter calcoaceticus*
      *Enterobacter aerogenes*
      *Enterobacter aglomerans* (I)
      *Enterobacter aglomerans* (II)
      *Escherichia coli*
      *Klebsiella pneumoniae*
      *Nisseria gonorrhoeae*
      *Proteus mirabilis*
      *Proteus morganii*
      *Proteus vulgaris*
      *Providencia* spp.
      *Pseudomonas*
      *Pseudomonas aeruginosa*
      *Pseudomonas fragi*
      *Salmonella choleraesuis*
      *Salmonella enteritidis*
      *Salmonella gallinarum*
      *Salmonella paratyphi* A
      *Salmonella schottmuelleri*
      *Salmonella typhimurium*
      *Salmonella typhosa*
      *Serratia marcescens*
      *Shigella flexnerie* Type II
      *Shigella sonnei*
      *Virbrio cholerae*
Viruses:
   Adenovirus Type IV

*Feline Pneumonitis*
*Herpes Simplex* Type I & II
HIV-1 (AIDS)
Influenza A (Japan)
Influenza A2 (Aichi)
Influenza A2 (Hong Kong)
Parinfluenza (Sendai)
Poliovirus
Reovirus
*Respiratory Synctia*

Fungi and Mold:
  *Alternaria alternata*
  *Asperigillus niger*
  *Aureobasidium pullulans*
  *Candida albicans*
  *Cladosporium cladosporioides*
  *Drechslera australiensis*
  *Gliomastix cerealis*
  *Microsporum audouinii*
  *Monilia grisea*
  *Phoma fimeti*
  *Pithomyces chartarum*
  *Scolecobasidium humicola*
  *Trychophyton interdigitale*
  *Trychophyton mentagrophytes*

The open literature and the prior art cited above do not teach topical application of aqueous solutions of organosilicon quaternary ammonium compounds to the skin, nor do they teach such application methods utilizing these compositions as being broad spectrum antimicrobial methods which remain on the skin, bond to the skin, are substantive to it and resist removal by washing or rinsings.

SUMMARY OF THE INVENTION

A number of aqueous hand lotion formulations containing solubilized quaternary ammonium organosilanes, suitable as antimicrobial hand sanitizers, antimicrobial skin cleansers, liquid antimicrobial hand soaps and antimicrobial skin moisturizing lotions have been prepared. The formulations disclosed in this instant invention impart both antimicrobial and moisturizing functionality to the skin. These functional characteristics remain on the skin throughout normal daily activities for up to sixty-four hours. All formulations contain organosilane quaternary ammonium compounds, specifically 3-(trimethoxysilyl)propyloctadecyldimethyl ammonium chloride, 3-(trimethoxysilyl)-propyldidecylmethyl ammonium chloride, the trisilanol derivatives and the polysiloxanol derivatives and mixtures thereof. Other quaternary ammonium organosilicon compounds, the silanol derivatives and mixtures thereof, such as 3-(trimethoxysilyl)-propyldimethyltetradecyl ammonium chloride, 3-(trimethoxysilyl)propyldimethylhexadecyl ammonium chloride, 3-(dimethoxymethylsilyl) propyldimethyloctadecyl ammonium chloride and 3-(methoxydimethylsilyl)propyldimethyloctadecyl ammonium chloride may also be employed, as would be apparent to those skilled in the art.

Prior art has failed to recognize that quaternary ammonium organosilanes containing hydrolyzable groups can form antimicrobially active, clear solutions in aqueous media which are stable over extended periods of time, which do not require addition of immiscible materials to form antimicrobially effective emulsions and also do not require adjustment of pH. The compositions of the present invention can be readily and easily prepared by adding the quaternary ammonium organosilane composition to purified semiconductor grade water. The addition of lower alcohols in up to 80 % concentration to lower the freezing point of the solution, to increase evaporation rates of the aqueous media from the skin, to increase the rate of antimicrobial effects, to enhance cleansing properties, or to increase solubility of other additives, does not affect the extended stability or performance of the solution. The preparative method of the present invention provides stable, clear, quaternary ammonium organosilane solutions. The solutions can be applied to human skin and animal skin to deposit on the treated skin an antimicrobially active quaternary ammonium organosilane derivative which is substantive to the skin, is not removed by subsequent rinsings, which retains its antimicrobial activity against a broad range of pathogens, will remain active on the skin for up to 64 hours and retards moisture loss from the skin.

The present invention provides methods for application of quaternary ammonium organosilane compositions to the skin and the disclosed compositions are readily applied to the skin when incorporated as ingredients in the amounts of 0.01 to 4.0 percent into carrier solutions. Carrier solutions as defined in the present invention are aqueous solutions or alcoholic water solutions. All formulations are homogeneous and may be scented and/or colored and may contain water-soluble additives to enhance performance and viscosity. The active quaternary ammonium organosilane ingredients are applied to the skin as liquid, fluid, gel or solid solutions. When applied to the skin, the quaternary ammonium organosilane species forms a molecular layer adjacent to and on the skin.

Prior art has demonstrated that deposition of organosilicon quaternary ammonium compounds onto substrates from aqueous solutions is achievable. It has also been extensively demonstrated that quaternary organosilicon ammonium compounds are effective against a broad spectrum of pathogens including gram positive and gram-negative bacteria, viruses and fungi, including molds and yeasts. On application to the skin, the organosilicon quaternary ammonium compounds form a water insoluble molecular layer, which is substantive to the skin and will remain through a minimum of nine rinses. Skin treated with the above described materials are resistant to infection from gram positive and gram negative bacteria, viruses, and fungi, including mold and spores. Application of these formulations promotes a smooth feeling to the skin and protects against redness and chapping due to the moisturizing qualities of the material.

Conversely, prior art has not demonstrated that aqueous solutions of the organosilicon quaternary compounds may be effectively applied to the skin where the quaternary ammonium organosilane moiety forms a polymeric network over the skin and is bonded to it, whether covalently, electrostatically or through hydrogen bonding. While on the skin it retains its antimicrobial character and is effective against the range of pathogens described above.

The compositions of the present invention are non-toxic, efficient and economical for use as topical antimicrobial skin-treatments. There are no reports of methods that teach aqueous solutions of quaternary ammonium organosilanes being applied as aqueous formulations to the skin for antimicrobial effect or purpose. The substantiveness, continuing antimicrobial activity and moisturizing qualities are new, novel and unprecedented. Conventional non-silicon containing quaternary ammonium compounds, when applied to the skin are easily removed by rinsing or hand washing. They exhibit no substantive characteristics on skin. Following application, organosilane quaternary ammonium compounds are substantive to the skin and exhibit antimicrobial activity while on the skin, reducing or eliminating existing pathogens and preventing reinfection by reducing or eliminating additional pathogens introduced after application. They do not demonstrate irritability to the skin presumably due to their unique bonding abilities which effectively places a barrier of organosiloxy moieties between the skin surface and the antimicrobial active ammonium cation. This antimicrobial barrier prevents reinfection on subsequent introduction of pathogens and functions as a moisturizing layer by slowing moisture loss from the surface of the skin.

Accordingly, in one embodiment, this invention provides a composition for antimicrobially treating human or animal skin that is comprised of an effective amount of the water soluble quaternary ammonium organosilane and an aqueous carrier.

In another embodiment, this invention provides a method to prepare a clear water-stable composition comprising the quaternary ammonium organosilane of this invention and water or a water and lower alcohol solution.

In a further embodiment, this invention provides a method of antimicrobially treating skin that consists of contacting the skin with an aqueous composition containing quaternary ammonium organosilanes for a period of time to sufficiently render the substrate antimicrobially active.

In addition, the present invention provides a method to treat skin and nails with the quaternary ammonium organosilane having adhered thereto.

In a further embodiment, the present invention provides a composition for a liquid antimicrobial skin cleanser comprising an aqueous solution of quaternary ammonium organosilanes and additives, and thickeners which when applied to the skin will cleanse the skin of dirt and oils and simultaneously deposit an antimicrobial molecular layer of quaternary ammonium organosilanes on the skin surface.

In yet another embodiment of this invention, a method is provided to prepare aqueous compositions containing quaternary ammonium organosilanes incorporating deionized-water with or without various described additives which may be colored or scented without decreasing the stability or antimicrobial character, efficacy or substantiveness when the composition is subsequently applied to the skin.

A further embodiment of the present invention provides a method and compositions for coating skin and nails with a quaternary ammonium organosilane which is antimicrobial, substantive to the skin and which is not removed by rinsing and washing.

In yet another embodiment of the present invention provides a method for treating skin that retards loss of moisture from the skin by its presence and bonded character to the skin and is a moisturizer for the skin.

Thus, the present invention provides a method for rendering skin, nails and hair antimicrobial, with a quaternary ammonium organosilane which adheres to the skin, hair and nails, retains its antimicrobial activity for up to 64 hours and prevents reinfection of the skin, hair and nails on subsequent contact with infection producing pathogens.

It is apparent to those skilled in the art that quaternary ammonium organosilanes may be incorporated into a variety of skin care products without the addition or presence of water immiscible additive oils, greases or waxes to enhance moisturizing qualities and impart substantive antimicrobial properties. These products include all solutions containing quaternary ammonium organosilanes that contact the skin and which do not contain water immiscible organic additives such as oils, waxes or greases.

Additional advantages and benefits of the intention are set forth in the description which follows and it is to be understood that the foregoing general description and the following detailed description are explanatory and are not restrictive of the invention as claimed.

DETAILED DESCRIPTION OF THE INVENTION AND SPECIFIC EMBODIMENTS

These and other advantages of the present invention are provided by a method of treating the skin, hair and nails with a stable aqueous solution in which all ingredients are miscible in water and which contains a quaternary ammonium organosilane which on application to the skin causes the quaternary ammonium organosilane to adhere and bond to the skin providing an antimicrobially active coating on the skin which is effective against a broad range of pathogens, remains antimicrobially active on the skin for extended periods, and slows moisture loss from the skin.

Quaternary ammonium organosilanes which can be used in the present invention vary widely in structure and include silanes represented by the formula:

$$A_{4-n}Si(R\ NH_aR^1_bZ)_n$$

wherein:

A denotes an alkoxy radical with 1 to 8 carbon atoms or an alkylether alkoxy radical with 2 to 10 carbon atoms, or an alkyl radical with 1 to 4 carbon atoms;

R denotes a divalent hydrocarbon radical with 1 to 8 carbon atoms;

$R^1$ denotes alkyl radicals with 1 to 12 carbon atoms: alkyl ether hydrocarbon radicals of 2 to 12 carbon atoms such as

—CH$_2$CH$_2$OCH$_3$ or —CH$_2$CH$_2$OCH$_2$CH$_2$CH$_3$;

hydroxy containing alkyl radicals of 1 to 10 carbon atoms such as

—CH$_2$CH$_2$OH or —CH$_2$CH$_2$CH$_2$CH(OH)CH$_3$; or hydrocarbon radicals of 1 to 10 carbons containing nitrogen such as —CH$_2$CH$_2$NH$_2$ or —CH$_2$CH$_2$N(CH$_3$)$_2$ a is 0, 1 or 2, b is 1, 2 or 3, and the sum of a and b is 3;

Z is an anion such as chloride, bromide, iodide, tosylate, hydroxide, sulfate or phosphate; and n is 1, 2 or 3.

The terminology used herein is for describing particular embodiments and is not intended to be limiting.

The term "alkyl" as used herein refers to a straight chain or branched saturated hydrocarbon.

The term "alkylether alkoxy" as used herein refers to an alkyl ether moiety containing carbon-oxygen-carbon bonds and having a terminal oxygen atom bonded to the silicon atom.

The term "alkyl ether" group as used herein refers to an alkyl group as defined above containing within the carbon chain a carbon-oxygen-carbon linkage. Polyethers are also included in this definition as being alkyl groups containing more than one carbon-oxygen-carbon linkage.

The term "alkoxy" as used herein refers to alkyl groups defined as above which have a terminal carbon-oxygen linkage. "Lower" used herein in reference to alkyl, alkoxy and alcohols, indicates species and compounds having 1 to 4 carbons.

The term "antimicrobial" as used herein is used in reference to the ability of the compound composition or article to eliminate, remove, inactivate, kill or reduce microorganisms such as bacteria, viruses, fungi, molds, yeasts and spores. The term antimicrobial as used herein to imply reduction and elimination of the growth and formation of microorganisms such as described above.

Specific quaternary ammonium organosilanes within the scope of the invention are represented by the formulae:

A requirement of the quaternary ammonium organosilanes used in this present invention is that they be soluble in water at ambient temperature (20–25° C.) to be useful. It has been observed that if the organosilanes are not sufficiently soluble in water to form a clear solution at ambient temperature in the quantities in which they are to be incorporated into the aqueous solutions, then the production of clear and stable solutions is precluded.

Another requirement for the practice of this invention is that the aqueous formulations and compositions described herein are prepared using purified water. Distilled or deionized water which when measured conductively has a resistance of at least 10 megohm per square centimeter with a purity level of 18 megohm per square centimeter is preferred. The presence of dissolved impurities such as metal ions, metal salt and anionic species, particularly fluoride ions will greatly decrease the stability and shelf life of the aqueous formulations.

The compositions suitable to practice the present invention contain from 0.01% to 5% by weight of the quaternary ammonium organosilanes described above whether admixed with water singly or jointly as in a mixture of the quaternary ammonium organosilanes. The preferred concentrations of the present invention are 0.1 to 4.0 weight percent. Lower concentrations do not maximize the antimicrobial benefits obtained on application and higher concentrations do not impart additional antimicrobial or moisturizing advantage. While any formulation may be used to cause the quaternary ammonium organosilanes to beneficially adhere to the skin, the most preferred are aqueous solutions containing 0.2 to 0.5 weight percent. Various water soluble additives and stabilizers as defined in prior art may be incorporated into solutions as practiced in this instant invention which does not change or alter the scope and novelty of this invention.

The preferred quaternary ammonium organosilanes of the present invention are the commercially available 3-(trimethoxysilyl)propyldimethyloctadecyl ammonium chloride and 3-(trimethoxysilyl)propyldidecylmethyl ammonium chloride. These materials contain hydrolyzable methoxy groups bound to the silicon atom. It is well known from prior art and to those skilled in the art that on addition of these compounds to water, the methoxy groups hydrolyze to form hydroxy substituted silicon atoms termed in the art as silanols with simultaneous liberation of methanol as a by-product of the hydrolysis. The resultant compound formed on addition of quaternary ammonium organosilanes of the above compositions are the respective trisilanol species for 3-(trimethoxysilyl)propyldimethyloctadecyl ammonium chloride and 3-(trimethoxysilyl)didecylmethyl ammonium chloride As the silanol species prepared on hydrolysis are reactive, they may undergo auto condensation reactions in aqueous solution to form water-soluble silanol containing disiloxane species represented by the following example structure obtained from 3-(trimethoxysilyl)propyldimethyloctadecyl ammonium chloride:

where Me=$CH_3$

These compounds may undergo further auto condensation reactions with additional trisilanol species present to produce water soluble polysiloxanol compounds which can be represented as follows for derivatives of the 3-(trimethoxysilyl)-dimethyloctadecyl ammonium chloride hydrolysis products:

where Me=$CH_3$

Additional water-soluble homologues may be present in the formulations and compositions of this invention. The trisilanol, disiloxanylsilanol and polysiloxanol derivatives are all equally reactive with the skin and bond to the skin on application with liberation of water to form a macromolecular network on the skin, nail and hair surface which is insoluble in water. The resultant polymeric molecular network adhering to and/or bonded to the skin obtained on application of the formulations of this invention derived from 3-(trimethoxysilyl)propyldimethyl-octadecyl ammonium chloride and 3-(trimethoxysilyl)propyldidecylmethyl ammonium chloride respectively, can be represented by the idealized formulas:

and where n is an integer of 1 to >1000.

It will be understood by those skilled in the art that these formulations when present on the skin, hair and nail substrate are three dimensional, cross-linked, water-insoluble, polymeric coatings which would be expected to contain some uncondensed silanol moieties. It is also expected that monomeric, dimeric and oligomeric species would be present on the skin following application of the aqueous quaternary ammonium organosilane solution, and these would bond to the skin, whether by covalent, electrostatic or hydrogen-bonding mechanisms and be substantive to the skin, and not removed by washing or rinsing.

The polysiloxane quaternary ammonium species formed on the skin retain their antimicrobial activity. They are substantive to the skin, insoluble in water and are not removed by rinsing or washing with water. The resultant polymeric coating obtained on application of the formulations of the present invention protects the skin from pathogenic infections, destroys pathogens which may subsequently come to reside on its surface and through its polymeric nature, acts as a skin moisturizer by hindering moisture loss from the skin surface.

It is well known from prior art and from studies performed within this present invention, quaternary ammonium organosilane species such as derived from 3-(trimethoxysilyl) propyldimethyloctadecyl ammonium chloride and 3-(trimethoxysilyl)propyldidecylmethyl ammonium chloride are effective when placed on a substrate against a wide range of pathogens, including gram positive bacteria, gram negative bacteria, viruses, fungi, mold, yeast and spores.

Formulations suitable for direct application of quaternary ammonium organosilanes to the skin consist of aqueous solutions, aqueous solutions containing lower alcohols, glycols, stabilizers, and scented and colored aqueous solutions. These formulations are suitable as antimicrobial hand and skin sanitizing solutions and gels, hand, facial and body soaps, conditioning soaps, waterless hand cleaners, shower gels, moisturizing lotions, rehydrating gels, sunscreen lotions and gels, burn gels and ointments, depilatory lotions, insect repellant sprays and lotions, shaving creams and gels, after shaves and colognes, liquid makeup, skin astringents, lip balm, cold sore creams and gels, burn, cut and skin abrasion solutions, baby care formulations, diaper wipes, antiperspirant/deodorant sprays and sticks. Additionally, such preparations would be expected to be used in applications such as hand and skin disinfectants for hospital applications, surgical preoperative skin treatments, moisturizers, skin and nail fungus preparations and other applications where topical antimicrobial skin treatment would be desirable and beneficial.

In addition to direct application and spray application of aqueous solutions containing quaternized organosilanes, application to the skin by absorbing the antimicrobial solutions of this invention onto polypropylene towelettes was found effective in transferring the quaternary ammonium organosilane to the skin.

Liquid soaps containing solutions of the quaternary ammonium organosilanes were found effective carriers for transference of the antimicrobial composition to the skin. A number of liquid soap solutions suitable for skin and hand care were formulated. They exhibited excellent lathering, solubility in water, dirt removal and cleansing of skin and were stable for greater than one year. Temperature cycling between 5 and 70° C. did not cause precipitation of the quaternary ammonium organosilane dissolved in the formulation. The formulation was determined to be an effective antimicrobial soap.

The following examples are illustrative of the present invention and are not to be considered as limiting the invention. In the examples, the following materials were used:

ODTA: Octadecyldimethyl(3-trimethoxysilyl)propyl ammonium chloride. Obtained from Wright Chemical Corp., Wilmington, N.C. as a 42% active material in methanol. This material may also be named as 3-(trimethoxysilyl) propyldimethyloctadecyl ammonium chloride. Also available as a 42% active material from Aegis Environmental Management, Inc., Midland, Mich. marketed as Dow Corning® 5700.

REQUAT: 3-(trimethoxysilyl)propyldidecylmethyl ammonium chloride. Obtained from Sanitized Inc., New Preston, Conn.; Requat 1977 as a 42% active material in methanol.

TDTA: 3-(trimethoxysilyl)propyltetradecyldimethyl ammonium chloride obtained from Gelest, Inc., Tullytown, Pa., Cat. No. SIT7090.0 as a 50% solution in methanol.

EXAMPLE 1

A formulation suitable for use as a hand sanitizing and skin disinfecting solution was prepared by chilling 50 liters of deionized water (18 megohm purity) to 20° C. en liters of SDA-3A ethanol was added over 5 minutes to the stirred water producing an exotherm raising the temperature to approximately 50° C. Cooling was maintained on the stirred vessel until the temperature reached 20° C. The stir rate was then increased and 165 g ODTA was added drop-wise over 10 minutes. Stirring and cooling was maintained to keep the temperature at 20° C. for 1 hour. The formulation was allowed to return to room temperature over 2 hours with stirring. A water-soluble scent (Vanilla; #4510-CBE-WS, Andrea Aromatics, Princeton, N.J.) was added to an approximate concentration of 0.008% of the total volume. The solution was passed through a 5-micron filter and packaged into containers suitable for spray application.

EXAMPLE 2

A formulation suitable for use as an antifungal and antibacterial skin spray was prepared by chilling 50 liters of deionized water (18 megohm purity) to 20° C. The chilled water was stirred with an overhead stirrer and 252 mL of ODTA was added drop-wise over 30 minutes. After addition was completed, a water-soluble scent (Rain Fresh; #2878-JAB, Andrea Aromatics, Princeton, N.J.) was added to a concentration of 0.01%. The clear solution was transferred to an HDPE container and packaged into smaller packages suitable for retail sales. Shelf-life studies demonstrated the product prepared in this manner had a shelf life, when stored at ambient temperature, greater than one year.

EXAMPLE 3

A solution prepared as in Example 1 was tested on human skin to determine the ability of aqueous formulations containing quaternary ammonium organosilanes to reduce bacteria present on skin. The testing and evaluation were performed by Day Break Environmental Corp. (Phoenix, Ariz.). Bacterial determinations and concentrations reported in colony forming units were performed by Aerotech Laboratories, Inc. (Phoenix, Ariz.). The hands of human subjects were used as test surfaces with the right hand being treated by spray application with the test solution prepared as in Example 1. The left hand was washed with a standard soap, but otherwise left untreated. Normal activities were maintained through the duration of the testing. Hand washing of treated or untreated skin was not performed after initial treatment. Swabs of approximately 100 square centimeters were taken from the skin of the right hand treated, and untreated, skin of the left hand at identical, predetermined intervals, sealed in plastic containers and recorded on Chain of Custody forms. The samples were cultured at 35° C. for 48 hours and enumerated for total bacteria. Results are reported in the following Table 1:

TABLE 1

Hand Bacterial Concentrations in Colony Forming Units

| Time (hours) | 0 | 1 | 2 | 4 | 8 | 16 | 32 | 64 |
|---|---|---|---|---|---|---|---|---|
| Untreated | 1620 | 280 | 90 | 360 | $2.8 \times 10^6$ | $9.2 \times 10^6$ | $11.0 \times 10^6$ | $128 \times 10^6$ |
| Treated | 510 | 80 | 130 | 60 | 65,000 | $4.6 \times 10^6$ | 59,000 | $1.7 \times 10^6$ |

Figure 1:
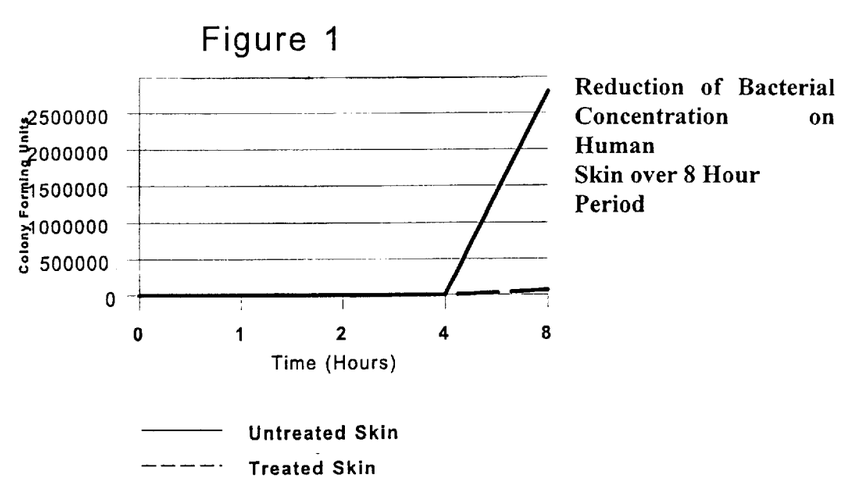
FIG. 1 is a graphical representation of the reduction of bacterial concentration on human skin over an 8 hour period.

The initial bacterial count ascertained as described above immediately following application of the quaternary ammonium organosilane solution was significantly lower, when compared to the bacterial count obtained from skin on the untreated left hand which was cleansed immediately prior to sampling with standard soap solution. Bacterial counts were approximately one third lower for the treated skin during the first hours of testing. At hour 2 treated skin was inoculated with bacteria from sneeze/cough which caused an average increase in total bacteria to slightly above that of the skin on the untreated hand. Bacterial collection and enumeration at hour 4 indicated decreased bacterial counts and emphasized the continuing antimicrobial activity of the treated skin. At 8 hours following initial application, total bacteria on untreated skin were approximately 43 times greater on the untreated skin when compared to the skin treated with the quaternized organosilane. (See FIG. 1).

Figure 2:
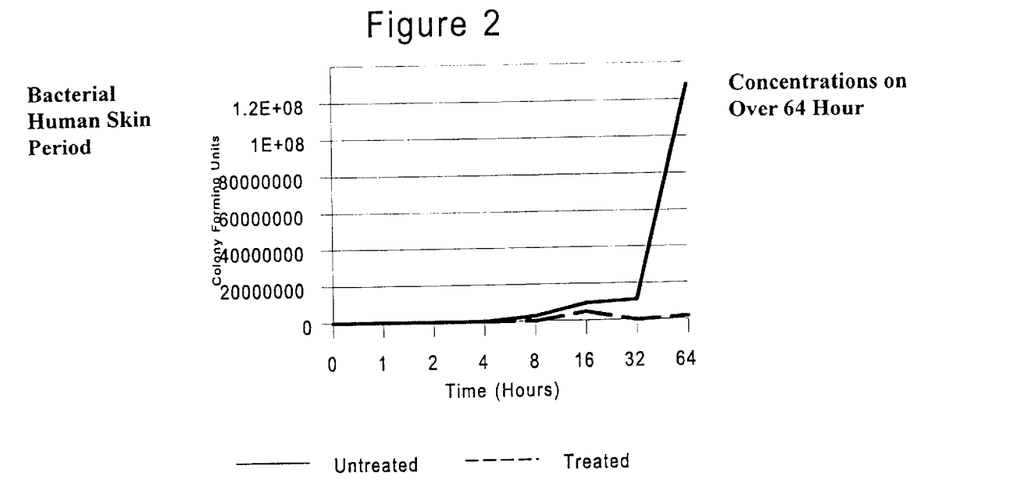
FIG. 2 is a graphical representation of bacterial concentration comparisons on human skin over 64 hours.

Testing was continued an additional 56 hours. At 16 hours after initial treatment of the skin with the quaternary ammonium organosilane solution, a vigorous, sweat-inducing workout was commenced. Bacterial levels were raised as expected, and were determined to be significantly higher on the untreated skin. Bacterial counts subsequent to the workout indicated lower bacteria levels than prior to the workout on the treated skin with untreated skin being approximately 200 times greater. Sweat induced by the workout did not remove the substantive quaternary ammonium organosilane treatment as evidenced by the decreasing bacterial counts collected from the treated skin. At the end of the test period, total bacteria present on the untreated skin was approximately 75 times greater than on the skin treated with the quaternary ammonium organosilane. During the course of the testing, sneezing on the treated skin was induced at two hours after initial application to increase bacterial levels. Measurements of bacterial colonies present on the treated skin following inoculation by the sneezing were found to be slightly elevated over the untreated skin. Microbial re-testing of the skin after two hours indicated bacteria to be at the lowest levels counted during the entire test. This result concludes that bacteria and other microbial pathogens introduced to skin previously treated with quaternary ammonium organosilanes are eliminated by the presence thereof. (See FIG. 2).

It is believed by the inventors that the antimicrobial activity of the quaternary ammonium organosilane present on the skin is decreased after extended exposure to bacteria by carcasses of dead or deactivated bacteria covering the organosilane surface adherent to the skin: The bacteria and other pathogens present must contact or closely approach the organosilane present on the skin surface to be effected. Contact with the treated skin is hindered or prevented by the presence of bacterial carcasses and detritus. Washing or rinsing of the treated skin to remove materials on the skin and expose the treated skin is expected to restore antimicrobial activity to the treated area.

EXAMPLE 4

A solution suitable for use as an antimicrobial skin formulation and as a base formulation to which other additives, fragrances or dyes could be subsequently added was prepared by charging a 20-liter stainless steel reaction vessel fitted with an overhead stirrer with 10 liters of 18 megohm purity deionized water. The water was stirred at ambient temperature (22° C.) as 72g of ODTA was added drop-wise over 20 minutes. The clear solution was stirred an additional 30 minutes. The material was stable for 18 months when stored in closed HDPE, glass or epoxide coated aluminum containers.

EXAMPLE 5

The antimicrobial effects of quaternary ammonium organosilanes were further demonstrated utilizing pig skin as a test substrate to approximate human skin. Testing was performed by Southern Testing & Research Laboratories, Inc. (Wilson, N.C.).

Samples of pig skin were obtained and cut to obtain approximately identical surface areas. One pig skin sample was treated with a solution as prepared in Example 1. Treatment of the pig skin sample was accomplished by wetting the surface by spray following which the sample was allowed to air dry. The treated pig skin and an identical sample of untreated pig skin were then tested for efficacy in eliminating and reducing *staphylococcus aureus*. Determinations were made using the dynamic shake flask method. The number of viable cells per milliliter of *staphylococcus aureus* for both treated and untreated samples of pig skin were determined at exposure times of 0, 10, 30 and 120 minutes with the following results:

TABLE 2

| Exposure (Minutes) | Untreated | Treated |
|---|---|---|
| 0 | $3.4 \times 10^6$ | $5.0 \times 10^6$ |
| 10 | $4.4 \times 10^6$ | $5.6 \times 10^6$ |
| 30 | $4.0 \times 10^6$ | $3.4 \times 10^6$ |
| 120 | $5.0 \times 10^6$ | 1 |

Numbers reported as viable cells per milliliter

Figure 3:
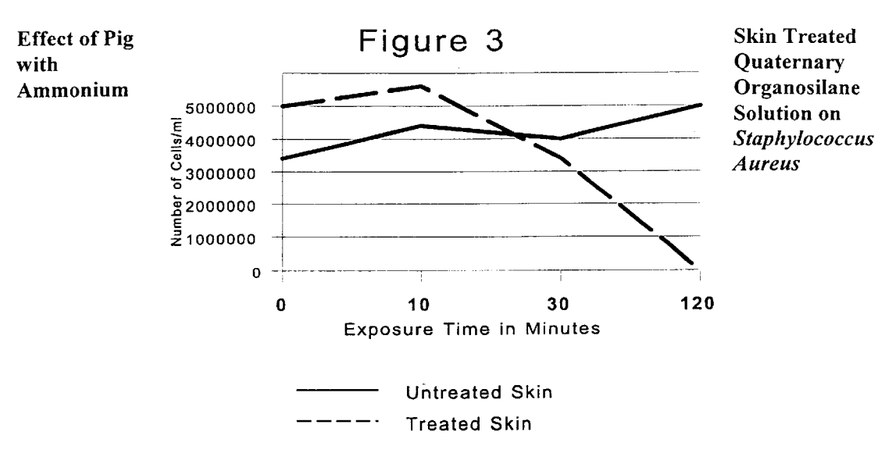
FIG. 3 is a graphical representation of the effect of pig skin treated with quaternary ammonium organosilane solution on *Staphylococcus Aureus*.

The number of reported viable cells of *staphylococcus aureus* increased steadily throughout the entire 120-minute exposure to the untreated pig skin, indicating no effect on the pathogen. Conversely, the addition of the treated pig skin to the *staphylococcus aureus* broth produced a slight rise in the number of viable cells counted per milliliter during the first 10 minutes. This was possibly caused by the replication rate of the *staphylococcus aureus* being greater than the rate of contact with the treated pig skin surface. After 30 minutes the number of viable cells were greatly reduced through contact with the treated pig skin. At the conclusion of the test and following 120 minutes of contact time with the treated pig skin, the number of viable cells were essentially annihilated as only a single viable cell per milliliter could be detected. This represents a reduction of 5 million viable cells per milliliter to essentially zero cells after 120 minutes contact time with pig skin containing quaternary ammonium organosilanes bonded to its surface. (See FIG. 3).

EXAMPLE 6

The novel substantiveness and resistance to removal by rinsing or washing of quaternary ammonium organosilanes applied to skin from an aqueous solution was demonstrated by the following procedure performed by Southern Testing & Research Laboratories, Inc. (Wilson, N.C.).

Pig skin samples, again chosen for its similar characteristics to human skin, were cut and determined to have approximately identical surface areas. The samples were then treated by spray with an approximately 0.1% active solution as prepared in Example 1. Following application, the pig skin samples were allowed to air dry and then individually subjected to a number of one second rinses with deionized water in an effort to remove the quaternized organosilane from the surface by dissolution. The minimum number of rinses was one and the maximum number of rinses was nine consecutive rinses on a single pig skin test sample. The amount of quaternary ammonium organosilane remaining on the surface was determined by measuring the reduction in the number of viable cells per milliliter of staphylococcus aureus after a 30 minute contact time utilizing the dynamic shake test method. In the tests, all samples performed identically in reducing the number of viable cells to $<10^4$ cells per milliliter over 30 minutes even though the initial test concentrations of staphylococcus aureus varied from 1 to 8 million cells per milliliter. A control sample in the form of an untreated sample of pig skin, when tested under identical conditions, allowed a significant increase of staphylococcus aureus. Results are reported in the following Table 3. as the number of viable cells per milliliter:

TABLE 3

| Number of 1 Second Water Treatments | Cell Count @ Time Zero | Cell Count after 30 minute Exposure |
| --- | --- | --- |
| 0 | $1.0 \times 10^6$ | $<1 \times 10^4$ |
| 1 | $2.5 \times 10^6$ | $<1 \times 10^4$ |
| 2 | $1.7 \times 10^6$ | $<1 \times 10^4$ |
| 3 | $8.0 \times 10^6$ | $<1 \times 10^4$ |
| 4 | $1.3 \times 10^6$ | $<1 \times 10^4$ |
| 5 | $1.1 \times 10^6$ | $<1 \times 10^4$ |
| 6 | $1.4 \times 10^6$ | $<1 \times 10^4$ |
| 9 | $4.1 \times 10^6$ | $<1 \times 10^4$ |
| Untreated | $1.0 \times 10^7$ | $1.2 \text{ V } 10^7$ |

Figure 4:
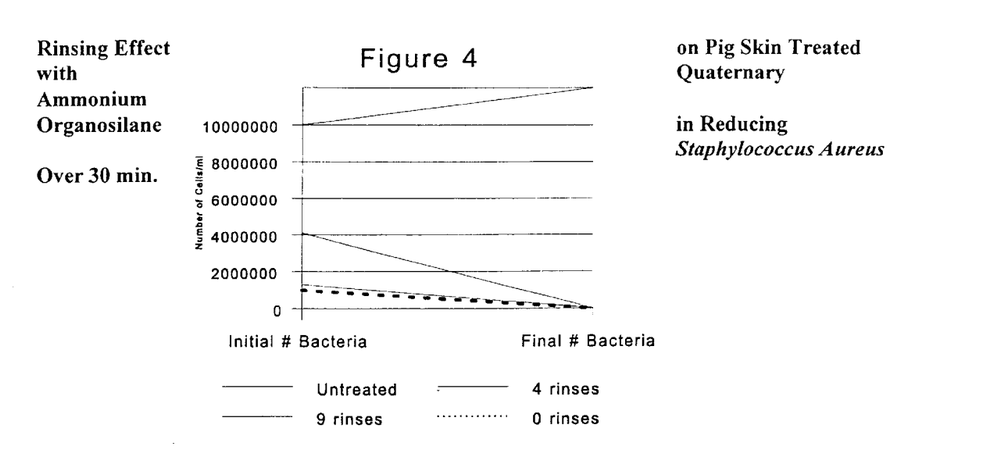
FIG. 4 is a graphical representation of the rinsing effect on pig skin treated with quaternary ammonium organosilane in reducing *Staphylococcus Aureus*.

This testing clearly indicates that quaternary ammonium organosilanes bond to skin, are substantive to it, are insoluble in water, are not removed by rinsing with water and retain antimicrobial activity after rinsing. The coating remaining on the skin after rinsing is as antimicrobially effective as pre-rinse compositions bonded to skin. (See FIG. 4).

EXAMPLE 7

Increasing antimicrobial effectiveness and efficiencies in pathogen removal by increasing the surface concentration of the quaternary ammonium organosilane moieties adhering to the skin surface was determined. A sample of pig skin was treated with 0.3 weight percent of the quaternized organosilane prepared as in Example 4. Application was by spray to wet the pig skin surfaces followed by an air dry of 2 hours. A sample of pig skin of approximately identical size was left untreated. The dynamic shake flask test method was employed to test both treated and untreated pig skin samples. Pathogen concentrations were determined at start and at 10, 30 and 120 minute intervals. Testing was performed by Southern Testing & Research Laboratories Inc. (Wilson, N.C.). Results are reported in Table 4 as the number of viable cells per milliliter follow:

TABLE 4

| Exposure (minutes) | Untreated | Treated |
| --- | --- | --- |
| 0 | $2.2 \times 10^6$ | $2.7 \times 10^6$ |
| 10 | $2.6 \times 10^6$ | $2.4 \times 10^6$ |
| 30 | $3.8 \times 10^6$ | $1.0 \times 10^6$ |
| 120 | $4.2 \times 10^6$ | 1 |

Figure 5:
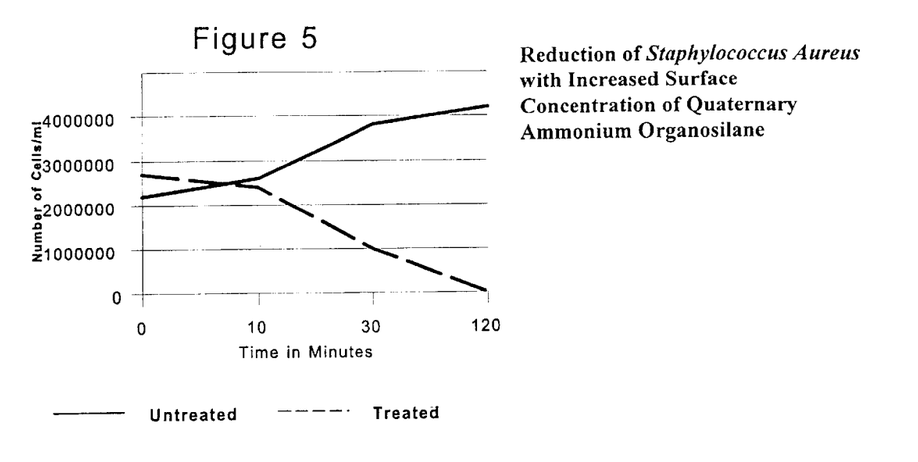
FIG. 5 is a graphical representation of *Staphylococcus Aureus* reduction with increased surface concentration of quaternary ammonium organosilanes.

The treated pig skin depleted the staphylococcus aureus to approximately zero in the test time of 120 minutes. The rise in pathogen levels noted in the preceding Example 6 which tested pig skin samples treated with a 0.1 weight percent active composition as prepared as in Example 1 did not occur when higher concentrations of the active material were employed to treat the pig skin sample. The rate of pathogen decrease was more rapid at the higher treatment concentration. Untreated pig skin permitted the staphylococcus aureus to increase steadily and significantly over the test period. (See FIG. 5).

EXAMPLE 8

A solution prepared as in Example 1 was utilized to prepare towelettes suitable for use as antimicrobial hand wipes. Polypropylene towelettes, approximately 5"×7", were moistened with 2 mL of solution, folded, placed in waterproof packets and sealed. After three months, the pouch was opened. Clean porcelain plates were wiped on one half of one side with the towelettes and allowed to dry. Measurement of the contact angle of water droplets on the surface of the porcelain plates indicated an average contact angle of 65° for the treated side and 43° for the untreated side. The higher contact angles indicate the presence of the quaternary ammonium organosilane on the plate surface. Washing the plate with deionized water following application of the quaternary ammonium organosilane did not change the contact angles as measured previously for the treated and the untreated plate surfaces. Similar experiments utilizing cotton or cellulose towelettes showed a marginal increase in contact angle after treatment of the plate surface with the towelette. This difference was due to the quaternary ammonium organosilane present in the aqueous solution being reduced through reaction with the cotton and cellulose towelettes and, therefore, was not available in solution to be transferred to the substrate.

EXAMPLE 9

A liquid antimicrobial hand soap formulation was prepared by adding 120 grams ODTA over a period of 10 minutes to a stirred solution of 15 liters deionized water (18 megohm purity) containing 30 ppm FD&C Yellow #6 while maintaining the reaction temperature at 25° C. To this solution was added over 30 minutes 5 kg of Burcoterge LHS (Burlington Chemical, Burlington, N.C.), a prepared formulation of liquid soap concentrate, Burcoterge LHS. The orange mixture was stirred for an additional 2 hours. The clear liquid solution was stable when stored at ambient temperatures for greater than one year and is suitable for use in liquid spray-soap applications.

EXAMPLE 10

To the formulation prepared as in Example 9 was added 1.5% sodium chloride, with mechanical stirring, over a period of 10 minutes. The formulation thickened immediately and was suitable for use as a clear liquid antimicrobial hand soap.

EXAMPLE 11

A clear liquid antimicrobial hand soap containing 14.4% actives with a pH of 5.5–6.5, a Gardner-color of 1 and a viscosity of 7300 cps at 25° C. was prepared utilizing the following materials and procedure obtained from Stepan Company (Northfield, Ill.). Deionized water (1956 g) was stirred with an overhead stirrer as Biosoft FF-600 (51 g), Amphosol CA (500 g), Ammonyx CDO Special (234 g), Ammonyx CO (99 g), Ninol LMP (60 g), Kessco PEG 6000 DS (30 g), disodium EDTA (6 g) and ODTA (60 g as a 42% solution in methanol) were added and stirred for 30 minutes. The mixture was then heated to 60–70° C. Mixing was then continued until all material had dissolved. The clear solution was cooled and the pH adjusted to 5.5–6.5 with citric acid. No salt addition was necessary to adjust viscosity. The material had a shelf life stability greater than one year. Stability and clarity were not effected when citric acid or disodium EDTA were deleted from the formulation.

EXAMPLE 12

Testing of the soap prepared in Example 11 for antimicrobial efficacy and substantiveness on the skin was performed by comparison tests on the hands of test subjects. Normal washing and rinsing of the right hand with the soap prepared in Example 11 was followed by air drying. The wash and rinse procedure was then repeated on the left hand with a non-bacterial bar soap and air dried. Testing for microbial contamination was performed by wiping an area of approximately 25 square centimeters on the back of the hands and the fingertips with cotton swabs moistened in deionized water. Sampling was performed at 0, 2, 6 and 24 hours following washing with normal daily activities being maintained. The swabs were then employed to inoculate 15×100 mm blood agar plates (tryptic soy agar with 5% sheep's blood) obtained from Hardy Diagnostics of Phoenix, Ariz. and incubated at 35° for 48 hours. Total bacterial count for both hands at time 0, immediately following washing, was determined to be approximately zero. The bacterial count for the hands washed with regular soap increased steadily over the course of the 24 hour test period. At the conclusion of the test period, bacterial counts for the hands washed with bar soap were an average of 150 times higher than bacterial counts obtained from hands washed with liquid soap containing the quaternary ammonium organosilane component.

EXAMPLE 13

To 15 liters of a stirred solution of deionized water containing 0.2% REQUAT and 30 ppm FD&C yellow #6 was added 5 kg. of a soap concentrate mixture containing sodium lauryl sulfate, cocamido propylbetaine, alkyl polyglycoside oligomeric and PEG-7 glyceryl cocoate, obtained from Henkel Corporation (Ambler, Pa.). Stirring was maintained at a temperature of 25° C. until dissolution of the soap concentrate was complete as determined by formation of a transparent solution. Stirring was continued for an additional 30 minutes before 1.5% by weight sodium chloride was added in portions over 15 minutes. The formulation was stirred an additional 30 minutes, filtered through a 10 micron filter and packaged into suitable containers.

EXAMPLE 14

An antimicrobial hand cleaner containing D-limonene (Aldrich Chemical Co., Milwaukee, Wis.) was prepared by mixing in a stainless vessel having overhead stirring 68.35 parts deionized 18 megohm purity water with 1 part sodium chloride. To this stirring solution was slowly added 0.2 parts Requat over a period of 20 minutes. Stirring was continued as a solution containing 25 parts Monamine 779 (Mona Industries, Paterson, N.J.) and 5.45 parts D-limonene were added slowly. Phosphoric acid was employed to adjust the pH.

EXAMPLE 15

To a vessel having good agitation was added 7.56 kg of deionized water and 2.0 kg. SD Alcohol 40-B. Stirring was continued until the temperature caused by the alcohol addition returned to 25° C. ODTA, 20 g, was added slowly over 15 minutes. To the clear solution and with continued agitation was added 100 g Phospholipid PTC, 20 g PEG-75 (Mona Industries, Paterson, N.J.) and 300 g propylene glycol (Aldrich Chemical Co., Milwaukee, Wis.). The solution was suitable for antimicrobial diaper wipe applications.

EXAMPLE 16

A facial cleanser containing a quaternary ammonium organosilane and suitable for sensitive skin applications was prepared by charging a kettle fitted with an overhead stirrer with 7.0 liters of deionized water having a purity of 18 megohm. The water was stirred as 200 grams ODTA was added over 15 minutes. Stirring of the clear solution was continued for an additional 30 minutes before 1.92 kg Plantaren PS200, 200 g Standamid LDS, 760 g Lamepon S and 100 g Cetiol HE (Henkel Corporation, Ambler, Pa.) were added sequentially. Stirring was continued until the mixture was homogeneous. Fragrance and color was then added and the pH adjusted to pH 6.2 to 6.8 with a solution of 50% citric acid.

EXAMPLE 17

A poultry industry disinfectant and sanitizer suitable for use with poultry industry workers was prepared by charging a vessel with 96 parts deionized water and 4 parts SIT7090.0, 3-(trimethoxysilyl)tetradecyl ammonium chloride (Gelest, Inc., Tullytown, Pa.).

EXAMPLE 18

An antimicrobial alcohol gel suitable for skin disinfection was prepared by stirring a solution containing 29.7 weight percent 18 megohm deionized water and 67.0 weight percent ethanol (90%) at room temperature as 0.3 weight percent ODTA was added slowly over 30 minutes. Sepigel 305 in an amount equal to 3.0 weight percent was added with mixing at moderate speed over 20 minutes. Stirring was continued until a clear, transparent gel was obtained.

EXAMPLE 19

A deodorizing antiperspirant spray was prepared by stirring a solution containing 46.85 parts 18 megohm deionized water, 10.00 parts propylene glycol and adding 0.1 parts ODTA over 15 minutes. To the stirred solution at room temperature was added 40.00 parts of a 50% solution of aluminum chlorohydrate, Lexein X250 and Bronopol-Boots (Inolex Chemical Co., Philadelphia, Pa.) over 20 minutes and stirred until clear. The solution was suitable for packaging into a lined aerosol container with fluorocarbon or carbon dioxide propellant.

It will be apparent to those skilled in the art that various changes, variations and modifications can be made in the present invention without departing from the spirit and scope of the invention. It is intended that the specifications and examples of this patent be considered as exemplary.

What is claimed is:

1. A method of reducing or eliminating the number of microorganisms on the surface of skin, hair or nails, said method comprising contacting said surface with a soap or spray comprised of an aqueous solution of a water-soluble quaternary ammonium organosilane in an amount effective to eliminate or inhibit the growth of said microorganisms, said quaternary ammonium organosilane having the formula:

$$A_{4-n}Si(R\ NH_a R^1{}_b Z)_n$$

wherein:
A is a member selected from the group consisting of alkoxy radicals of 1 to 8 carbon atoms, alkylether alkoxy radicals of 2 to 10 carbon atoms, and alkyl radicals with 1 to 4 carbon atoms;
R is a divalent hydrocarbon radical with 1 to 8 carbon atoms;
$R^1$ is a member selected from the group consisting of alkyl radicals with 1 to 12 carbon atoms, alkyl ether hydrocarbon radicals of 2 to 12 carbon atoms, hydroxy-containing alkyl radicals of 1 to 10 carbon atoms, and nitrogen-containing hydrocarbon radicals of 1 to 10 carbon atoms, wherein the nitrogen atom has three bonds;
a is 0, 1 or 2, b is 1, 2 or 3, and the sum of a and b is 3;
Z is a member selected from the group consisting of chloride, bromide, iodide, tosylate, hydroxide, sulfate and phosphate; and n is 1, 2 or 3, and wherein: the aqueous solution is free of water-insoluble oil carriers, and does not contain non-silicon quaternary ammonium compounds.

2. A method in accordance with claim 1 in which $R^1$ is a member selected from the group consisting of —$CH_2CH_2OCH_3$ and —$CH_2CH_2OCH_2CH_2CH_3$.

3. A method in accordance with claim 1 in which $R^1$ is a member selected from the group consisting of —$CH_2CH_2OH$ and —$CH_2CH_2CH_2CH(OH)CH_3$.

4. A method in accordance with claim 1 in which $R^1$ is a member selected from the group consisting of —$CH_2CH_2NH_2$ and —$CH_2CH_2N(CH_3)_2$.

5. A method in accordance with claim 1 in which said quaternary ammonium organosilane is present at a concentration of from about 0.01% to about 20% by weight.

6. A method in accordance with claim 1 in which said quaternary ammonium organosilane is 3-(trimethoxysilyl) propyldimethyloctadecyl ammonium chloride.

7. A method in accordance with claim 1 in which said quaternary ammonium organosilane is 3-(trimethoxysilyl) propyldidecylmethyl ammonium chloride.

8. A method in accordance with claim 1 in which said quaternary ammonium organosilane is 3-(trimethoxysilyl) propyldimethyltetradecyl ammonium chloride.

9. A method in accordance with claim 1 wherein the soap or spray comprises a mixture of said quaternary ammonium organosilanes.

10. A method in accordance with claim 1 in which said microorganisms are members selected from the group consisting of gram-positive and gram-negative bacteria.

11. A method in accordance with claim 1 in which said microorganisms are viruses.

12. A method in accordance with claim 1 in which said microorganisms are fungi.

13. A method in accordance with claim 1 in which said microorganisms are a member selected from the group consisting of algae and mold.

14. A method in accordance with claim 1 in which said microorganisms are yeast.

15. A method in accordance with claim 1 in which said microorganisms are spores.

16. A method in accordance with claim 1, wherein the soap or spray comprises water-soluble additives.

17. A method in accordance with claim 1 in which the amount of said aqueous solution and said quaternary ammonium organosilane therein is sufficient to maintain said reduction or elimination of pathogens for 64 hours.

18. A method in accordance with claim 16 in which said water-soluble additives are members selected from the group consisting of methyl alcohol, ethyl alcohol, and propyl alcohol, and constitute from 1% to 80% of said aqueous solution.

19. A method in accordance with claim 1 in which said soap is in the form of a gel.

20. A method in accordance with claim 1 in which said soap is a solid.

21. A method in accordance with claim 1 in which said quaternary ammonium organosilane constitutes 00.1 to 4 weight percent of said soap or spray.

22. A method in accordance with claim 16 in which said water-soluble additives comprise a dye at 0.001 to 0.2 weight percent of said soap or spray.

23. A method in accordance with claim 16 in which said water-soluble additives comprise a scent at 0.001 to 1.0 weight percent of said soap or spray.

* * * * *